United States Patent [19]

Butner

[11] Patent Number: 4,583,860
[45] Date of Patent: Apr. 22, 1986

[54] OPTICAL MULTIPLE SAMPLE VACUUM INTEGRATING SPHERE

[75] Inventor: Cyrus L. Butner, Arlington, Va.

[73] Assignee: The United States of America as represented by the Administrator of the National Aeronautics and Space Administration, Washington, D.C.

[21] Appl. No.: 556,481

[22] Filed: Nov. 30, 1983

[51] Int. Cl.[4] ............... G01N 21/47; G01N 21/01
[52] U.S. Cl. ................................. 356/446; 250/228;
356/73; 356/236; 356/244
[58] Field of Search ............ 356/446, 445, 447, 448,
356/236, 73, 244, 372, 246; 250/228, 308, 358.1

[56] References Cited

U.S. PATENT DOCUMENTS

| | | | |
|---|---|---|---|
| 2,707,900 | 5/1955 | Maresh et al. | 356/236 |
| 2,821,103 | 1/1958 | Blet | 356/236 X |
| 3,277,773 | 10/1966 | White | 250/228 |
| 3,520,660 | 7/1970 | Webb | 356/246 X |
| 3,545,871 | 12/1970 | Waska | 356/236 |
| 3,572,951 | 3/1971 | Rothwarf | 356/448 |
| 3,847,024 | 11/1974 | Beever et al. | 73/432 |
| 3,874,799 | 4/1975 | Isaacs et al. | 356/236 X |
| 3,951,721 | 4/1976 | Ishibai et al. | 250/228 X |
| 3,998,551 | 12/1976 | Suga | 356/73 |
| 4,012,144 | 3/1977 | Hedelman | 356/73 |
| 4,101,222 | 7/1978 | Mathisen | 356/244 |
| 4,120,582 | 10/1978 | DeVries et al. | 356/73 |
| 4,232,971 | 11/1980 | Suga | 356/446 |
| 4,360,268 | 11/1982 | Zucker et al. | 356/73.1 |
| 4,487,504 | 12/1984 | Goldsmith | 250/228 x |
| 4,540,286 | 9/1985 | Satake et al. | 356/445 |

Primary Examiner—Vincent P. McGraw
Assistant Examiner—Robert D. V. Thompson, III
Attorney, Agent, or Firm—John O. Tresansky; John R. Manning; Ronald F. Sandler

[57] ABSTRACT

An integrating sphere (10) comprised of a uniform diffusely reflecting spherical cavity (24) having mutually transverse input and output ports (42, 46) and a linear sample transport mechanism (12) secured thereto so that the multiple samples (136) can be brought into registration with the input port, one at a time, without having to open or disassemble the apparatus when a change of a sample (136) is desired. A vacuum tight seal (72) is provided between the cavity (24) and transport mechanism (12) for maintaining the integrity of a vacuum generated within the sphere when attached to source of optical energy. The device is utilized, for example, to test the emissive characteristic such as the relative fluorescence quantum efficiency of a dye sample placed in the path of a monochromatic optical energy source coupled to the input port (42) while having a light detector coupled to the output port (46).

5 Claims, 6 Drawing Figures

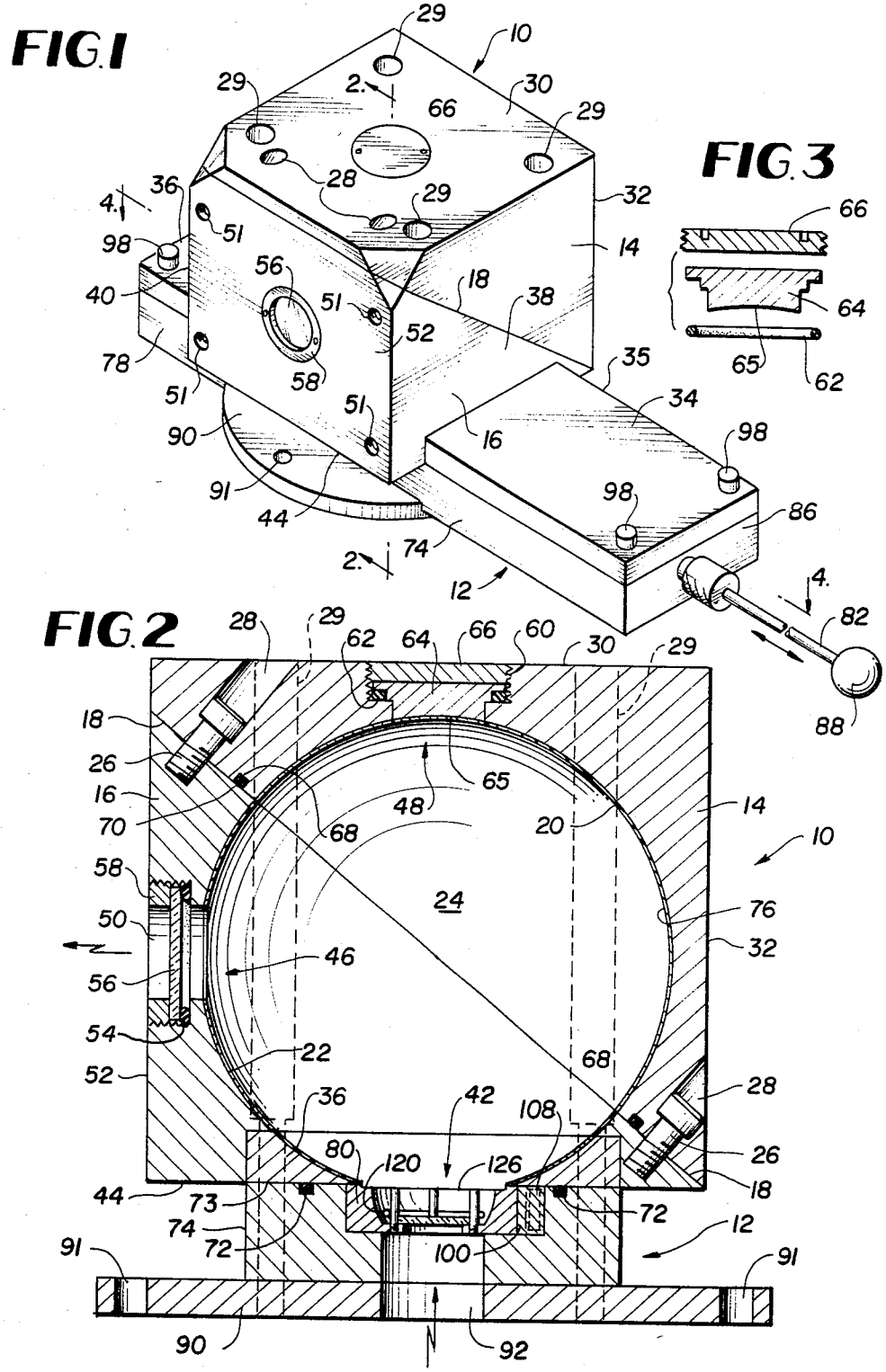

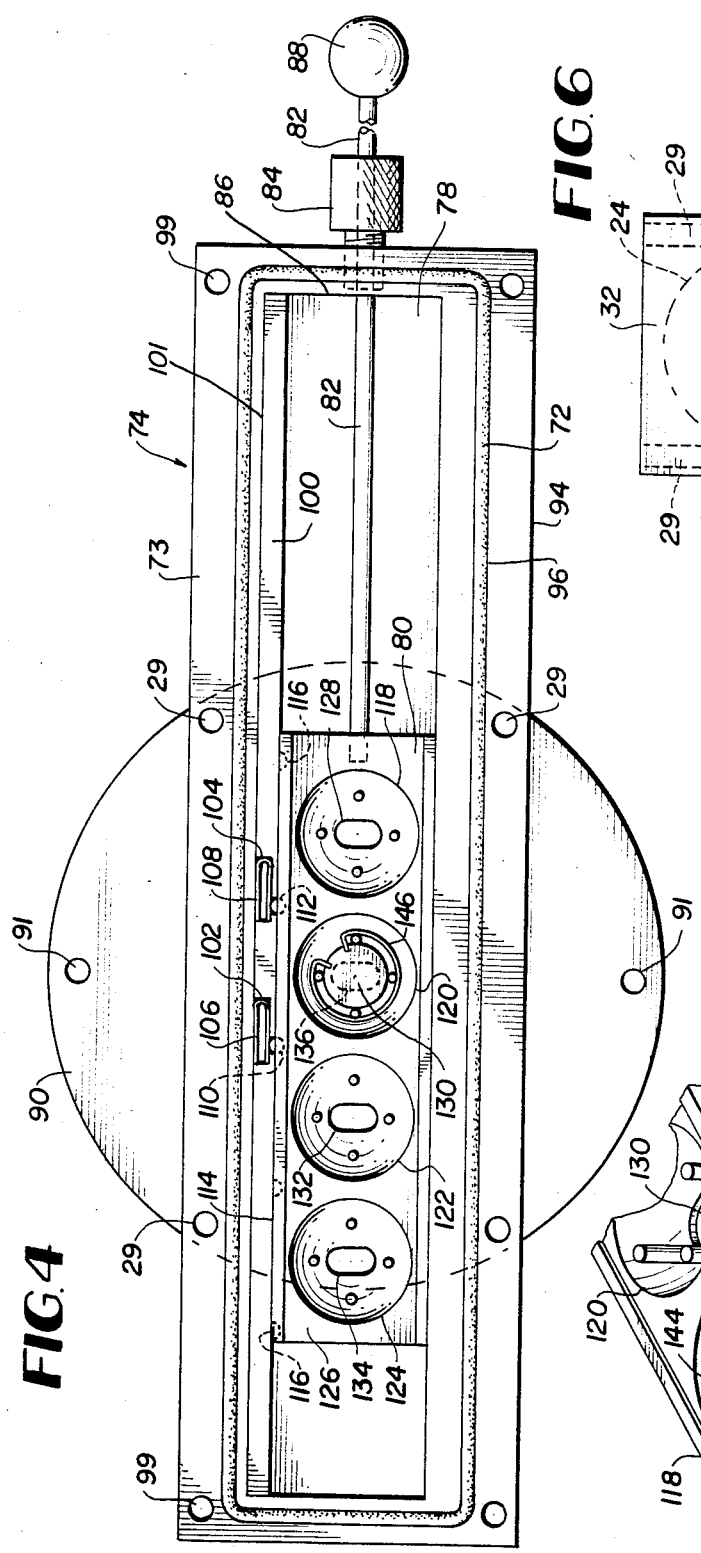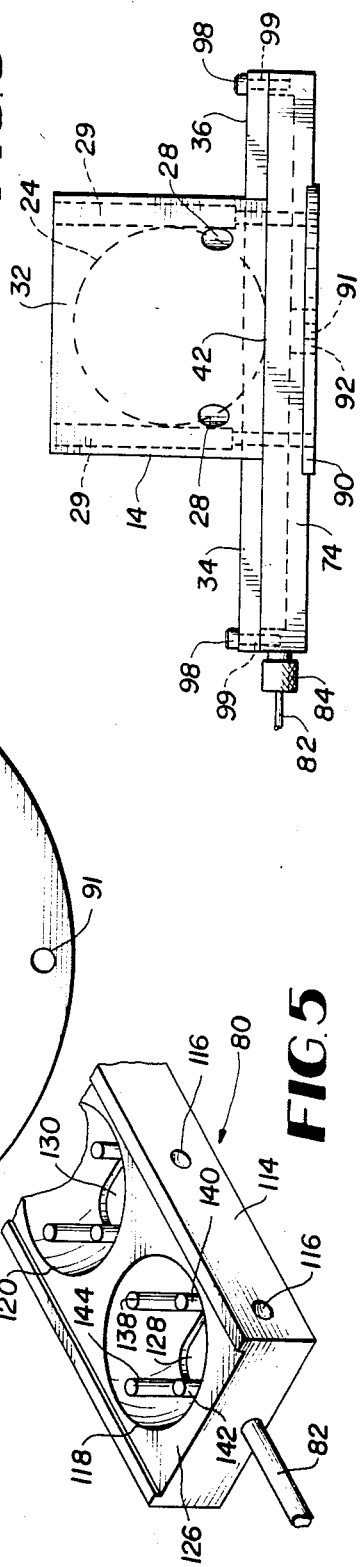

OPTICAL MULTIPLE SAMPLE VACUUM INTEGRATING SPHERE

ORIGIN OF THE INVENTION

The invention described herein was made by an employee of the United States Government and may be manufactured and used by or for the Government for governmental purposes without the payment of any royalties thereon or therefor.

TECHNICAL FIELD

The invention relates generally to apparatus for making optical radiometric measurements and more particularly to an evacuated integrating sphere and sample transport mechanism for measuring the emissive characteristics of a plurality of samples selectively placed in the path of a monochromatic optical energy source.

BACKGROUND ART

An integrating sphere is a well known device for providing a uniform light source and essentially comprises a spherical cavity with two ports and whose inner surface is coated with uniform, diffusely reflecting, white paint. One port allows light to enter the cavity, the other allows light to exit the cavity and be observed by a light detector. In many applications involving an integrating sphere, it is of interest to place a sample inside the cavity so that the light coming through the entrance port can strike it causing it to emit light which is then collected and observed. By producing multiple internal diffuse reflections, the integrating sphere provides uniform irradiation of the exit port irrespective of the direction in which light is emitted from the sample. A light detector placed at the exit port, therefore, sees a uniform spectral radiance that is proportional to the spectral flux emitted from the sample.

STATEMENT OF THE INVENTION

Accordingly, it is an object of the present invention to provide an improvement in apparatus for making optical radiometric measurements.

Another object of the invention is to provide an improvement in apparatus for making optical radiometric measurements with an integrating sphere.

Still another object of the invention is to provide an improvement in optical radiometric measurement apparatus made with an integrating sphere on a plurality of samples.

A further object of the invention is to provide an improvement in optical radiometric measurement apparatus including an integrating sphere where a plurality of samples are utilized in sequence under a vacuum without the need to open the sphere and break the vacuum in the course of changing samples.

These and other objects are achieved by means of an integrating sphere and a linear transport mechanism which are coupled together and having a vacuum tight seal therebetween. The inner surface of the spherical cavity is coated with a uniform diffusely reflecting white paint and includes an input port and at least one output port. The output port is adapted to be coupled to an externally located optical detector while the input port is situated adjacent a generally rectangular multiple sample holder which is slidably located in an elongated channel of a container housing of the transport mechanism and through which a rod passes for moving the sample holder back and forth beneath the input port.

The container housing, moreover, includes a circular mounting plate for coupling to an optical energy source, such as a monochromator, and includes a central aperture for coupling optical energy to a sample in registration with the input port of the integrating sphere which then fluoresces and directs fluorescent energy into the spherical cavity which then uniformly exits the output port to the detector. In its preferred form, the integrating sphere additionally includes a second output port preferably opposite the input port which can either be blocked or opened upon demand.

The foregoing as well as other objects, features and advantages of the invention will become apparent from the following detailed description when taken in conjunction with the accompanying drawings.

BRIEF DESCRIPTION OF THE DRAWINGS

FIG. 1 is a perspective view which is illustrative of the preferred embodiment of the invention;

FIG. 2 is a central axial view of the embodiment shown in FIG. 1 taken along the lines 2—2 thereof;

FIG. 3 is an exploded view of the parts included in the sub-assembly forming a plug for one of the output ports shown in FIG. 2;

FIG. 4 is a cross sectional view of the embodiment shown in FIG. 1 taken along the lines 4—4 thereof;

FIG. 5 is a fragmentary perspective view partially illustrative of the construction of the sample holder shown in FIGS. 2 and 4; and FIG. 6 is a rear planar view, reduced in size, of the embodiment shown in FIG. 1.

DETAILED DESCRIPTION OF THE INVENTION

Referring now to the drawings and more particularly to FIG. 1, the embodiment of the invention disclosed therein is comprised of two major components, namely; an integrating sphere 10 and a multiple sample transport mechanism 12.

As shown in FIG. 1, the integrating sphere is comprised of two body members 14 and 16 which are joined together along a diagonal surface 18 to form a generally rectangular block type configuration which houses a spherical cavity which is illustrated in FIG. 2. Each of the body members 14 and 16 have hemispherical inner surfaces 20 and 22 which when joined together form an integrating spherical cavity 24. The two body members 14 and 16 are held together along the diagonal surface 18 by four threaded bolts 26, two of which are placed into holes 28 drilled in the top surface 30 and two of which are placed into holes 28 drilled in side surface 32 of the body member 14. This is shown in FIGS. 2 and 6. The body member 16 includes a relatively thick generally rectangular metal plate 35, portions 34 and 36 of which project outwardly from the side walls 38 and 40 to provide a unitary mounting flange for the sample transport mechanism 12. Further the two body members 14 and 16 have four equally spaced holes or bores 29 which are adapted to receive bolts for attaching the entire assembly to an optical energy source.

The spherical cavity 24 as shown in FIG. 2 includes an input port 42 which is formed in the lower portion of the hemispherical surface 22 of the body member 16 so that it is located at the center of the bottom wall 44 which is welded to the mounting flange 35. The integrating sphere cavity 24 additionally includes at least one output port 46 which is located in surface 22 of the body member 16 and is disposed at right angles relative to the input port 42. Although not essential, a second output port 48 is provided in the preferred embodiment of the invention and comprises a port located directly opposite from the input port 42.

As shown, the first output port 46 also includes a threaded bore 50 formed in the side wall 52 of the body member 16 to accommodate an O-ring seal 54, a circular glass window 56, and a retaining ring 58. The second output port 48 is formed in the hemispherical surface 20 of the body member 14. The output port 48, moreover, includes a threaded bore 60 which is adapted to accommodate an O-ring seal 62, a solid metal plug 64 having a curved inner surface 65 matching the spherical surfaces 20 and 22 and a threaded circular cap 66. The three members 62, 64 and 66 are furthermore shown in exploded view in FIG. 3. However, when desirable, the plug 64 and the cap 66 can be deleted in favor of a second window 56 and a retaining ring 58 presently associated with the first output port 46.

The integrating sphere cavity is adapted to be evacuated when coupled to an optical energy source, not shown, and the integrity of the vacuum within the entire assembly is maintained not only by the O-ring seals 54 and 62, but also by means of a larger O-ring seal 68 located in a groove 70 formed in the diagonal surface 18 of the body member 14 as well as an O-ring seal 72 formed in the top surface 73 of a container housing 74 as shown in FIGS. 2 and 4 and which forms part of the assembly comprising the transport mechanism 12.

The spherical cavity 24 as shown in FIG. 2 is sprayed with a white paint to provide a diffusely reflecting spherical surface 76 so as to reflect a beam of optical energy which is uniform to the output ports 46 and 48 by producing multiple internal diffuse reflections from any light energy entering the input port 42. The composition of the paint typically comprises a barium sulfate-polyvinyl alcohol paint formulation whose basic composition, as described in *Formulation Procedure And Spectral Data For A Highly Reflecting Coating From 200 nm–2300 nm*, Charles M. Shai, et al., NASA X-762-71-266, (July, 1971), is as follows: (1) barium sulfate-(55.2% by weight); (2) distilled water - (27.2% by weight); (3) polyvinyl alcohol, 99% hydrolyzed - (0.4% by weight); and (4) ethyl alcohol, absolute - (17.2% by weight). As many as 10 coats of this paint are sprayed onto the hemispherical surfaces 20 and 22 of the cavity bodies 14 and 16 as well as the curved inner surface 65 of the plug 64. Additionally, this paint is sprayed onto the inner surface of the sample holder, to be described, which faces into the reflecting cavity 24 via the input port 42.

Turning attention now to the sample transport mechanism 12, FIG. 1 discloses the general shape of this apparatus. As further illustrated in FIGS. 2 and 4, the container housing 74 comprises an elongated structure which is bolted to the bottom surface of the flange 35 which is welded to the bottom wall 44 of the cavity body member 16. It should also be pointed out that the container housing 74 is offset from the input port 42 of the spherical cavity 24 so that a sample holder 80 as shown in FIG. 4 can be shifted completely to one side of the input port 42 when desired. This accordingly necessitates that the linear dimension of the flange portion 34 be longer than that of the flange portion 36. The sample holder 80 is slidably located in an elongated channel 78 as shown in FIG. 4 and is adapted to be translated or moved within the container housing 74 by means of a metal rod 82 which extends through a vacuum feed through 84 located in the end wall 86. A knob 88 is attached to the end of the rod 82 so that it may be manually grasped by an operator who can then selectively position the sample holder by a pushing or pulling action indicated at FIG. 1.

Beneath the generally rectangular container housing 74 is located a circular mounting plate 90 having six mounting holes 91 located near the edge, four of which are aligned with the holes as shown in FIG. 4, so that the entire assembly can be secured with a vacuum tight fit to a source of optical energy, such as a monochromator, not shown. As shown in FIG. 4, six equally spaced mounting holes are thus provided. The mounting plate 90, moreover, includes a generally circular central aperture 92 as shown in FIG. 2 which is aligned with the input port 42 of the integrating sphere cavity 24.

The interior of the container housing 74 and its contents are best shown in FIG. 4 with the details of sample holder 80 being further disclosed in FIG. 5. Referring now to FIG. 4, the elongated rectangular channel 78 formed in the housing body 94 is surrounded by a peripheral groove 96 formed in the surface 73 which is adapted to receive the O-ring seal 72 previously mentioned. The O-ring seal 72 is adapted to provide a vacuum tight seal when the container housing 74 is bolted to the flange plate 35 by means of bolts 98 (FIG. 1) inserted into the holes 99. The channel 78 is adapted to not only receive the sample holder 80, but also a relatively thin insert bar 100 which extends the entire length of the channel 78 and which is positioned along one side 101 thereof. The insert bar 100 furthermore includes two vertical slots 102 and 104 which are each adapted to receive a folded metal spring element 106 and 108 and one ball bearing, the bearings being identified by reference numerals 110 and 112. The ball bearings 110 and 112 project through small holes in the side of the insert bar 100 so that they make contact with the side 114 of the sample holder 80 which additionally includes a plurality, namely five, indentations 116 which conform to the size of the ball bearings. The indentations 116 and the spring biased ball bearings located in the slots 102 and 104 form a detent assembly for establishing five fixed positions or stops of the sample holder 80 relative to the input port 42 of the integrating sphere.

With respect to the construction of the sample holder 80, it is comprised of a generally rectangular slide member having four concave hemispherical depressions or cups 118, 120, 122 and 124 formed in the surface 126 which is oriented toward the input port 42 (FIG. 2). At the bottom of each cup 118, 120, 122 and 124 is located a generally rectangular aperture having rounded end portions and being identified by reference numerals 128, 130, 132 and 134. The apertures 128 . . . 134 comprise openings which are adapted to permit optical energy entering the aperture 92 to impinge on a sample carried by a transparent circular sample plate or disc positioned between the input aperture 92 and the input port 42. One sample plate is shown in FIG. 4 by reference numeral 136. The sample plates which are locatable in the cups 118 . . . 124 are set into place between four small outwardly projecting positioning posts 138, 140, 142 and 144 as shown in FIG. 5. Each sample plate, moreover, is held snugly in place by means of a respective retaining ring 146 which is adapted to fit around the positioning posts but having two inwardly projecting end portions which make contact with the outer perimeter of the sample plate.

The top surface 126, the concave hemispherical cavities or cups 118, 120, 122, 124 and the respective positioning posts 138, 140, 142 and 144 of the sample holder 80, are additionally all spray painted with the same diffusely reflecting paint sprayed on the two hemispherical cavity surfaces 20 and 22 of the integrating sphere cavity 24. Thus all sample holder surfaces facing into the cavity 24 are colored white and match the diffusely reflecting surface of the cavity.

With respect to the materials used in fabricating the various parts of this invention, aluminum or brass may be utilized but brass is preferable, particularly for the container housing 74, the sample holder 80, and the insert bar 100 where sliding contact is encountered. Also the contact surfaces should be appropriately treated to prevent galling and binding with a minimum amount of outgassing.

In operation, a sample placed on a sample plate 136 is located between the positioning posts of any or all of the four concave sample holder cups 118, 120, 122 and 124, then a retaining ring such as shown in reference numeral 146 is slipped around the post and over the sample to hold it snugly in place. Once the sample holder 80 is loaded with samples, it is placed in the channel 78 of the container housing 74 and the positioning rod 82 is attached to it through the vacuum feed through 84. The two halves of the integrating sphere comprising the body members 14 and 16 are then screwed together and placed over the container housing 74 as shown in FIG. 1 so that it is completely covered, whereupon the four bolts 98 secure the flanged plate 35 to the container housing. Once the integrating sphere window 56 is secured by the retaining ring 58, the entire assembly is ready to be mounted onto a monochromator or other type of light source by bolts, not shown, inserted through holes 29 and 91 (FIG. 4) and the entire assembly is thereafter evacuated. An external light detector, not shown, is then attached to the window side 52 of the integrating sphere body member 16 by means of four threaded screw holes 51. The samples are then manually positioned one at a time within the optical axis of the incident radiation by moving the feed through rod 82 backwards and forwards. When desirable, the sample holder 80 can be moved completely out of the incident radiation by pulling the rod 82 out to the last detent position. The invention is primarily adapted to accommodate dye samples, for example, which have been placed on circular discs 136 and which fluoresce upon receiving incident radiation. The light of fluorescence then enters the cavity where it is integrated to provide uniform irradiation of the output port 46 where it is then detected.

Although the structure of the invention as disclosed is primarily used in connection with an internal vacuum for applications involving incident radiation of a very short wavelength (ultraviolet) which is greatly attenuated in an atmosphere, it can, however, be used without a vacuum when desirable.

Thus what has been shown and described is a combination of an integrating sphere and a linear sample transport assembly containing a plurality of samples which can be held under a vacuum while the exterior is maintained at normal room conditions. Secondly, the sample holder can accommodate up to four samples and its position within the container housing can be adjusted from outside of the housing so as to expose one sample at a time to the interior of the integrating sphere and the path of the incident radiation without interrupting the integrity of the vacuum.

Having thus shown and described what is at present considered to be the preferred embodiment of the invention, all modifications, changes and alterations coming within the spirit and scope of the invention as defined in the appended claims are herein meant to be included.

I claim:

1. Apparatus for making optical radiometric measurements on a plurality of samples, comprising, in combination:

integrating sphere means (10) including a spherical cavity (24) having a uniform reflecting surface (76), and input port (42) for coupling optical energy from an optically irradiated sample (136) into said cavity (24), and at least one output port (46) for coupling optical output energy uniformly from said cavity to optical detector means;

sample transport means (12) secured to said integrating sphere means (10) and having means (90) for being attached to a source of incident optical radiation and including an elongated container housing (74) having a central aperture (92) aligned with said input port (42), said housing having a lengthwise channel (78) formed therein for receiving a movable sample holder (80), said sample holder having a plurality of sample receiving means (118, 120, 122, 124) and respective apertures (128, 130, 132, 134) formed therein which are adapted to be selectively placed in alignment with said central aperture (92) and said input port (42) upon movement of said sample holder (80), and means (82) for translating said sample holder (80) linerally within said channel (78) whereby plural samples (136) respectively positioned in said sample receiving means are placed in the path of incident radiation from said source, one at a time;

a vacuum seal (72) between said sample transport means (12) and said integrating sphere means (10); and said output port (46) including an optical output window (56) and a vacuum seal (54) whereby a vacuum tight output port is provided and the entire appartus may be evacuated and radiometric measurements can be made on said samples (136) under a vacuum by translation of said sample holder (80) without the need to interrupt the vacuum while placing individual samples (136) in the path of incident radiation.

2. The apparatus as defined by claim 1 wherein said output port (46) is located mutually transverse of said input port (42).

3. The apparatus as defined by claim 2 and further including another vacuum tight output port (48) located in said integrating sphere (10) directly opposite said input port (42).

4. The apparatus as defined by claim 3 wherein said another vacuum tight output port (48) includes, an opening in said cavity (24), a vacuum seal (62) and a plug member (64) inserted in said sphere means (10) for closing said output port (48), and wherein said plug member (64) has a uniform inner reflecting surface (65) matching the surface (76) of said spherical cavity (24).

5. The apparatus as defined by claim 3 and wherein said another vacuum tight output port (48) includes, an opening in said cavity (24), an optical window (56) and a vacuum seal (62) for coupling optical energy out of said spherical cavity (24).

* * * * *